(12) United States Patent
Hashimoto et al.

(10) Patent No.: US 11,737,658 B2
(45) Date of Patent: Aug. 29, 2023

(54) MANIPULATOR ARM AND PATIENT-SIDE SYSTEM FOR SURGICAL SYSTEM

(71) Applicants: KAWASAKI JUKOGYO KABUSHIKI KAISHA, Kobe (JP); MEDICAROID CORPORATION, Kobe (JP)

(72) Inventors: Yasuhiko Hashimoto, Kobe (JP); Toshiaki Yoshida, Kobe (JP); Kazunori Suga, Kobe (JP)

(73) Assignees: KAWASAKI JUKOGYO KABUSHIKI KAISHA, Kobe (JP); MEDICAROID CORPORATION, Kobe (JP)

( * ) Notice: Subject to any disclaimer, the term of this patent is extended or adjusted under 35 U.S.C. 154(b) by 866 days.

(21) Appl. No.: 16/726,241

(22) Filed: Dec. 24, 2019

(65) Prior Publication Data
US 2020/0205645 A1 Jul. 2, 2020

(30) Foreign Application Priority Data

Dec. 26, 2018 (JP) .................................. 2018-243446
Dec. 17, 2019 (JP) .................................. 2019-227262

(51) Int. Cl.
*A61B 1/00* (2006.01)
*A61B 34/00* (2016.01)
(Continued)

(52) U.S. Cl.
CPC ........ *A61B 1/00149* (2013.01); *A61B 1/0016* (2013.01); *A61B 34/71* (2016.02);
(Continued)

(58) Field of Classification Search
CPC ... A61B 1/00149; A61B 1/0016; A61B 34/37; A61B 34/34; B25J 17/00; B25J 18/00
See application file for complete search history.

(56) References Cited

U.S. PATENT DOCUMENTS 7,955,322 B2  6/2011  Devengenzo et al.
8,182,470 B2  5/2012  Devengenzo et al.
(Continued)

FOREIGN PATENT DOCUMENTS

JP   H2-31942 U    2/1990
JP   H6-49962 Y2   12/1994
(Continued)

*Primary Examiner* — Mallika D Fairchild
*Assistant Examiner* — Naveed R. Kolia
(74) *Attorney, Agent, or Firm* — METROLEX IP LAW GROUP, PLLC

(57) ABSTRACT

A surgery manipulator arm according to an embodiment may include an arm body and a translation mechanism provided to a distal end portion of the arm body. The translation mechanism includes: a proximal side unit connected to the distal end portion of the arm body; a distal side unit including a tool holding part to which a surgical tool is attached; a connection unit connecting the proximal and distal side units; and an electrical wiring circuit electrically connecting the proximal and distal side units. The connection unit includes first and second pulleys; and a belt member wound around the first and second pulleys. The proximal and distal side units are attached to first and second attachment positions of the belt member such that the distal side unit moves in a direction opposite to a direction in which the proximal side unit moves in association with movements of the belt member.

20 Claims, 7 Drawing Sheets

(51) Int. Cl.
*B25J 9/00* (2006.01)
*B25J 17/00* (2006.01)
*B25J 18/00* (2006.01)
*A61B 34/30* (2016.01)
*A61B 34/37* (2016.01)

(52) U.S. Cl.
CPC ............ *B25J 9/0009* (2013.01); *B25J 17/00* (2013.01); *B25J 18/00* (2013.01); *A61B 34/37* (2016.02); *A61B 2034/305* (2016.02)

(56) References Cited

U.S. PATENT DOCUMENTS

| | | |
|---|---|---|
| 8,469,947 B2 | 6/2013 | Devengenzo et al. |
| 8,641,700 B2 | 2/2014 | Devengenzo et al. |
| 8,672,922 B2 | 3/2014 | Loh et al. |
| 8,888,764 B2 | 11/2014 | Devengenzo et al. |
| 9,050,119 B2 | 6/2015 | Devengenzo et al. |
| 9,480,533 B2 | 11/2016 | Devengenzo et al. |
| 9,486,288 B2 | 11/2016 | Devengenzo et al. |
| 2012/0209292 A1 | 8/2012 | Devengenzo et al. |
| 2013/0081489 A1 | 4/2013 | Fang et al. |
| 2014/0163581 A1* | 6/2014 | Devengenzo ............ B25J 15/04 606/130 |
| 2014/0171965 A1 | 6/2014 | Loh et al. |
| 2017/0079730 A1 | 3/2017 | Azizian et al. |
| 2017/0172676 A1 | 6/2017 | Itkowitz et al. |
| 2017/0367782 A1 | 12/2017 | Schuh et al. |
| 2018/0042688 A1 | 2/2018 | Devengenzo et al. |
| 2018/0117759 A1 | 5/2018 | Hasuo |
| 2019/0069964 A1 | 3/2019 | Hagn |

FOREIGN PATENT DOCUMENTS

| | | |
|---|---|---|
| JP | H11-123675 A | 5/1999 |
| JP | 2010-253162 A | 11/2010 |
| JP | 2011-45500 A | 3/2011 |
| JP | 2017-513550 A | 6/2017 |
| JP | 2017-515524 A | 6/2017 |
| JP | 2018-69370 A | 5/2018 |
| WO | 2017/147353 A1 | 8/2017 |

\* cited by examiner

MANIPULATOR ARM AND PATIENT-SIDE SYSTEM FOR SURGICAL SYSTEM

CROSS REFERENCE TO RELATED APPLICATIONS

This application claims priority to Japanese Patent Application No. 2018-243446 filed on Dec. 26, 2018 and Japanese Patent Application No. 2019-227262 filed on Dec. 17, 2019, the entire contents of each of which are incorporated herein by reference.

BACKGROUND

The disclosure may relate to a manipulator arm and a patient-side system to be used in a surgical system.

There has been known a master-slave type surgical system that includes multiple manipulator arms and performs surgery by moving the manipulator arms based on operation of a surgeon (for example, see Documents 1 and 2). In such a system, a surgical tool is attached to a distal end portion of each of the manipulator arms, and each of the attached surgical tools is translationally (straightly) moved by a translation mechanism. In light of the surgical safety, it may be preferable that the surgical tool is pulled out of a patient by only the translational movements of the translation mechanism. However, if the longitudinal length of the translation mechanism is large, the translation mechanism may get in the way during the surgery preparation or the surgery.

There has been known a manipulator in which a translation mechanism, which is configured to translationally move a surgical tool attached to a distal end portion of a manipulator arm, includes a base link, an idle link, and a carriage link which are expandable (for example, see Document 3).

Document 1: Published Japanese Translation of PCT International Application No. 2017-515524
Document 2: Published Japanese Translation of PCT International Application No. 2017-513550
Document 3: U.S. Pat. No. 8,182,470

That is, Document 3 discloses the translation mechanism which is expandable (contractable). The translation mechanism disclosed in Document 3 has room for improvement with respect to the linear movement speed of the surgical tool. Further, in the translation mechanism disclosed in Document 3, rotation shafts D to G to drive the surgical tool is driven by cables. This makes the structure of the translation mechanism complicated.

An object of an aspect of one or more embodiments in the disclosure may be to provide a surgical manipulator arm for a surgical system including a translation mechanism capable of a quick linear movement of a surgical tool. Another object of an aspect of one or more embodiments in the disclosure may be to provide a surgical manipulator arm capable of driving a surgical tool with an uncomplicated configuration.

An aspect of one or more embodiments may be a surgery manipulator arm that may include: an arm body including a plurality of links and a plurality of joints; and a translation mechanism provided to a distal end portion of the arm body. The translation mechanism includes: a proximal side unit connected to the distal end portion of the arm body; a distal side unit including a tool holding part to which a surgical tool is attached and which includes a motor configured to drive the surgical tool; a connection unit connecting the proximal side unit and the distal side unit; and an electrical wiring circuit electrically connecting the proximal side unit and the distal side unit. The connection unit includes a first pulley; a second pulley; and a belt member wound around the first and second pulleys and moveable in a first direction from the first pulley toward the second pulley and a second direction opposite to the first direction. The proximal side unit is attached to the belt member at a first attachment position, and the distal side unit is attached to the belt member at a second attachment position in such a manner that the distal side unit moves in a direction opposite to a direction in which the proximal side unit moves in association with movements of the belt member.

An aspect of one or more embodiments may be a patient-side system for a surgery system that may include: a manipulator arm; a wheeled base configured to hold the manipulator arm. The manipulator arm comprises: an arm body including a plurality of links and a plurality of joints; and a translation mechanism provided to a distal end portion of the arm body. The translation mechanism includes: a proximal side unit connected to the distal end portion of the arm body; a distal side unit including a tool holding part to which a surgical tool is attached and which includes a motor configured to drive the surgical tool; a connection unit connecting the proximal side unit and the distal side unit; and an electrical wiring circuit electrically connecting the proximal side unit and the distal side unit. The connection unit includes a first pulley; a second pulley; and a belt member wound around the first and second pulleys and moveable in a first direction from the first pulley toward the second pulley and a second direction opposite to the first direction. The proximal side unit is attached to the belt member at a first attachment position, and the distal side unit is attached to the belt member at a second attachment position in such a manner that the distal side unit moves in a direction opposite to a direction in which the proximal side unit moves in association with movements of the belt member.

According to at least one of the aspects described above, it may be possible to improve the linear movement speed of the surgical tool while preventing complication of the configuration of the translation mechanism.

An object, characteristics, and advantages of the invention may be apparent from the detailed descriptions of the one or more embodiments below with reference to the accompanying drawings.

DETAILED DESCRIPTION

Figure 1:
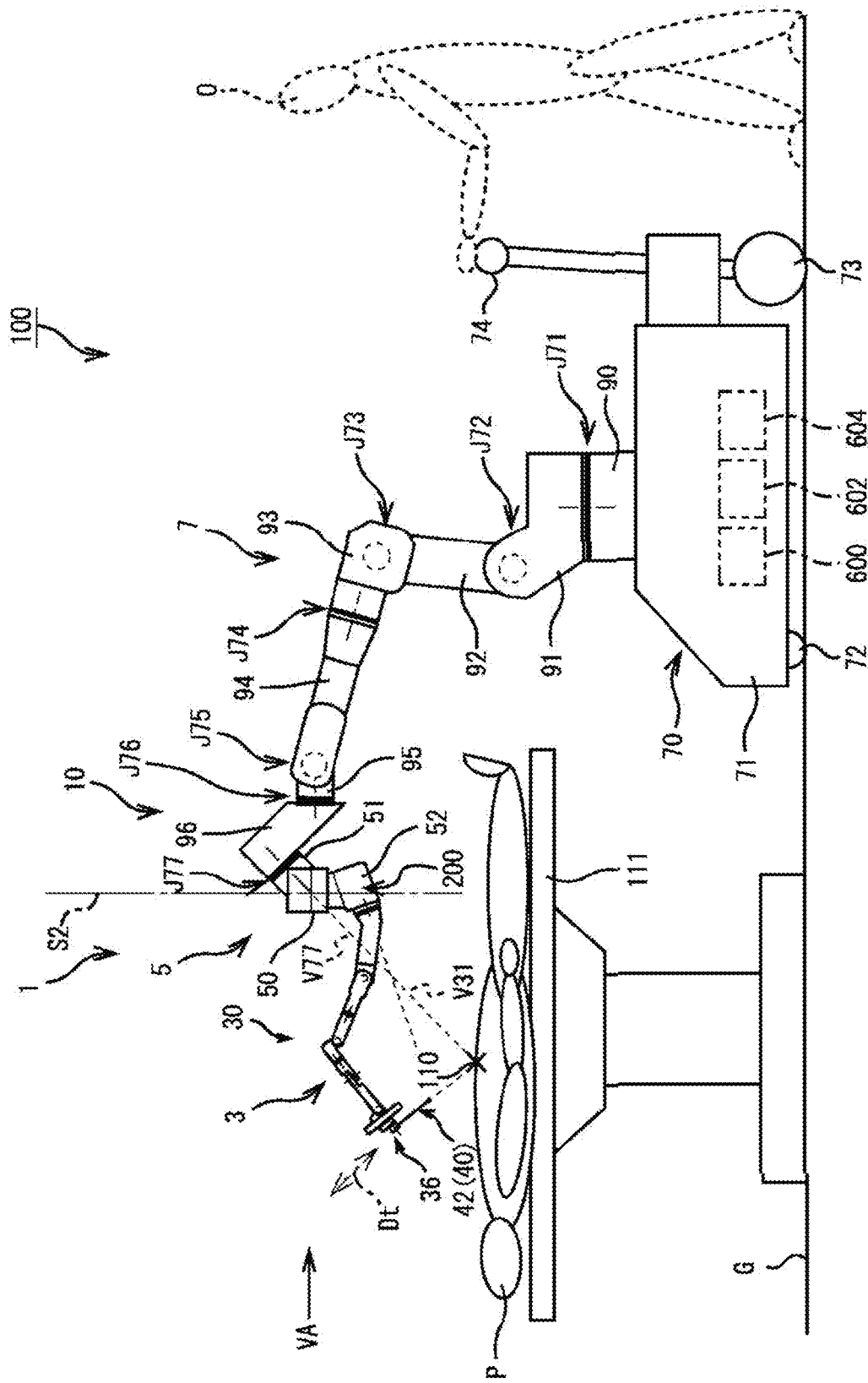
FIG. 1 is a diagram illustrating a schematic view of an overall configuration of a surgical system including a translation mechanism according to one or more embodiments.

Descriptions are provided hereinbelow for one or more embodiments based on the drawings. The invention is not limited to the one or more embodiments. In the respective drawings referenced herein, the same or equivalent constituents are designated by the same reference numerals and duplicate explanation concerning the same or equivalent constituents is omitted. All of the drawings are provided to illustrate the respective examples only.

FIG. 1 is a diagram illustrating a schematic view of an overall configuration of a surgical system in which a translation mechanism is provided according to one or more embodiments. A surgical system 100 is a system for a surgeon such as a doctor to perform endoscopic surgery on a patient P with a patient-side system 1, like robotic-assistant surgery and robotic telesurgery. In FIG. 1, the ratio of the size of the illustrated manipulator arms 3 to the positioner 7 is different from the actual ratio.

The surgical system 100 includes the patient-side system 1 and an operation apparatus 2 serving as an instruction apparatus (see FIG. 4 described later) for controlling the manipulator arms 3 of the patient-side system 1. The operation apparatus 2 is disposed apart from the patient-side system 1, and the patient-side system 1 is remotely controlled by the operation apparatus 2 during procedure. The surgeon inputs an action to be executed by the patient-side system 1 to the operation apparatus 2, and the operation apparatus 2 transmits the action instruction to the patient-side system 1. The patient-side system 1 receives the action instruction transmitted from the operation apparatus 2. Based on the action instruction, the patient-side system 1 operates a surgical tool 40 including an elongated shaft included in the patient-side system 1.

The operation apparatus 2 is an apparatus constructing an interface between the surgical system 100 and the surgeon so as to control the patient-side system 1. The operation apparatus 2 is disposed nearby or away from an operating table 111 (a surgical bed) in a surgery room or disposed outside of the surgery room. Although it is not illustrated, the operation apparatus 2 includes operation input units such as an operation manipulator arm and an operation pedal for the surgeon to input the action instruction, and a monitor that displays an image captured by an endoscope assembly (not illustrated) as the surgical tool 40 attached to the patient-side system 1. The surgeon operates the operation input units to input the action instruction to the operation apparatus 2 while visually checking an affected area (a surgery site 110) through the monitor. The action instruction inputted to the operation apparatus 2 is transmitted to the later-described controller 600 of the patient-side system 1 through wired or wireless communications.

The patient-side system 1 constructs an interface between the surgical system 100 and the patient P. In the surgery room, the patient-side system 1 is disposed nearby the operating table 111 on which the patient P is laid. Inside of the surgery room is sterilized to be a sterile field.

The patient-side system 1 includes the positioner 7, the arm base (platform) 5 attached to the distal end portion of the positioner 7, and the patient-side manipulator arms (hereinafter, simply referred to as "arms 3") detachably attached to the arm base 5. The positioner 7 is a device extending from a base to connect the base with the arm base 5. In this embodiment, the positioner 7 is formed as a multi-axis robot. The positioner 7 can move the position of the arm base 5 three-dimensionally with respect to a movable wagon 70, which is the base. The arm 3 and the arm base 5 are covered with a sterile drape(s) (not-illustrated) and shielded from the sterile field in the surgery room.

The distal end portion of each of the arms 3 is configured as a tool holding part 36 that can hold the surgical tool 40 and drive the surgical tool 40. The distal end portion of one of the arms 3 holds the endoscope assembly (not illustrated). The distal end portion of the rest of the arms 3 detachably holds an instrument 42. Hereinafter, the arm 3 to which the endoscope assembly is attached may be referred to as a "camera arm," and the arm 3 to which the instrument 42 is attached may be referred to as an "instrument arm." The patient-side system 1 in this embodiment includes four arms 3 including one camera arm and three instrument arms.

In the above-described patient-side system 1, the arm base 5 serves as a "hub" that is a base of the arms 3. In this embodiment, the positioner 7 and the arm base 5 form a manipulator arm support body 10 that movably supports the arms 3. Note that the positioner 7 may not be a multi-axis robot. For example, the positioner 7 may be a linear rail to support the arm base 5, a lifting and lowering device to support the arm base 5, or a bracket attached to a ceiling or a wall to support he arm base 5. The base to which the positioner 7 is connected is not limited to a movable configuration such as a wagon 70 or a wheeled base. For example, the base may be a wall or floor of the surgery room, or a stationary member that is fixed to the wall or the floor of the surgery room.

In the above-described patient-side system 1, the elements from the positioner 7 to the endoscope assembly or the instrument 42 are connected in series. In this disclosure, in each of the series of elements, an end portion closer to the positioner 7 (more specifically, an end portion closer to a base 90 that is a connection portion between the positioner 7 and the wagon 70) is referred to as a "proximal end portion," and an end portion on the opposite side is referred to as a "distal end portion."

The wagon 70, the positioner 7, the arm base 5, and the manipulator arms 3 are described in detail below.

As illustrated in FIG. 1, the wagon 70, serving as a wheeled base, includes a wagon body 71, front wheels 72 and rear wheels 73, and a handle 74. The front wheels 72 and the rear wheels 73 are rotatably attached to the wagon body 71, and the wagon body 71 is thus configured to be movable. The rear wheels 73 are configured to be turnable about a rotational axis of the handle 74, and this makes it possible to change a traveling direction of the wagon body 71 with the surgeon or a surgical assistant O grasping and turning the handle 74 about the rotational axis.

Operation of the patient-side system 1 is controlled by the controller 600. The controller 600 is formed of a computer such as a microcontroller, for example. The controller 600 and a storage 602 in which a control program and various kinds of data used for the operation control are stored are housed inside the wagon body 71. The wagon body 71 is also provided with an operation unit 604, which is mainly for setting and inputting the position and orientation of the positioner 7, the arm base 5, and the arms 3 before procedure (the later-described preparation orientation). The operation unit 604 is formed of a touch panel and the like, for example.

The positioner 7 includes the base 90 attached to the wagon body 71 and positioner link portions subsequently connected with each other from the base 90 toward the distal end portion. With one positioner link portion rotatably connected to another positioner link unit subsequently, the positioner 7 forms multiple joint portions. The positioner link portions include a first link 91 to a sixth link 96. The joint portions include a first joint J71 to a seventh joint J77.

Each of the joint portions in this embodiment is formed of a joint having a rotation axis; however, at least one or more of the joint portions may be formed of a direct-acting joint.

More specifically, the proximal end portion of the first link 91 is connected to the distal end portion of the base 90 with the first joint J71 as a roll joint arranged therebetween The proximal end portion of the second link 92 is connected to the distal end portion of the first link 91 with the second joint J72 as a pivotal (pitch) joint arranged therebetween. The proximal end portion of the third link 93 is connected to the distal end portion of the second link 92 with the third joint J73 as a pivotal joint arranged therebetween. The proximal end portion of the fourth link 94 is connected to the distal end portion of the third link 93 with the fourth joint J74 as a roll joint arranged therebetween. The proximal end portion of the fifth link 95 is connected to the distal end portion of the fourth link 94 with the fifth joint J75 as a pivotal joint arranged therebetween. The proximal end portion of the sixth link 96 is connected to the distal end portion of the fifth link 95 with the sixth joint J76 as a roll joint arranged therebetween. A positioner attachment portion 51 of the arm base 5 is connected to the distal end portion of the sixth link 96 with the seventh joint J77 as a roll joint arranged therebetween. Thus, the positioner 7 is formed as a multi-axis joint (seven-axis joint) arm having the multi-degree of freedom (seven degrees of freedom).

As described above, in the sixth link 96 as a positioner link portion attached to the positioner attachment portion 51 of the arm base 5, both the sixth joint J76 as a joint portion on the proximal end side and the seventh joint J77 as a joint portion on the distal end side are formed as the roll joints. In addition, the rotation axis of the sixth joint J76 is relatively inclined with respect to the rotation axis of the seventh joint J77. More specifically, the rotation axis of the sixth joint J76 is inclined with respect to the longitudinal direction of the sixth link 96, while the rotation axis of the seventh joint J77 is orthogonal to the longitudinal direction of the sixth link 96. An extension of the rotation axis of the sixth joint J76 and an extension of the rotation axis of the seventh joint J77 cross each other. That is, the surface of revolution of the sixth joint J76 is inclined with respect to the surface of revolution of the seventh joint J77.

The arm base 5 includes an arm base body 50, the positioner attachment portion 51 that is attached to the top (on the proximal end side) of the arm base body 50 with the distal end portion of the positioner 7 attached to the positioner attachment portion 51, and at least one arm attachment portion 52 that is attached to the bottom (on the distal end side) of the arm base body 50 with the proximal end portions of the arms 3 attached to the at least one arm attachment portion 52. The arm base 5 is configured to be relatively rotatable with respect to the distal end portion of the positioner 7 (the sixth link 96) about the rotation axis V77 of the seventh joint J77, serving as an arm base rotation axis V77. In this embodiment, multiple (four) arm attachment portions 52 are provided in accordance with the multiple (four) arms 3. Bases 80 of the arms 3 are respectively secured to the arm attachment portions 52. Thus, the proximal end portion of each arm 3 (the later-described first link 81) is configured to be relatively rotatable about a rotation axis V31 of the later-described first joint J31, serving as an arm proximal end rotation axis V31.

Figure 2:
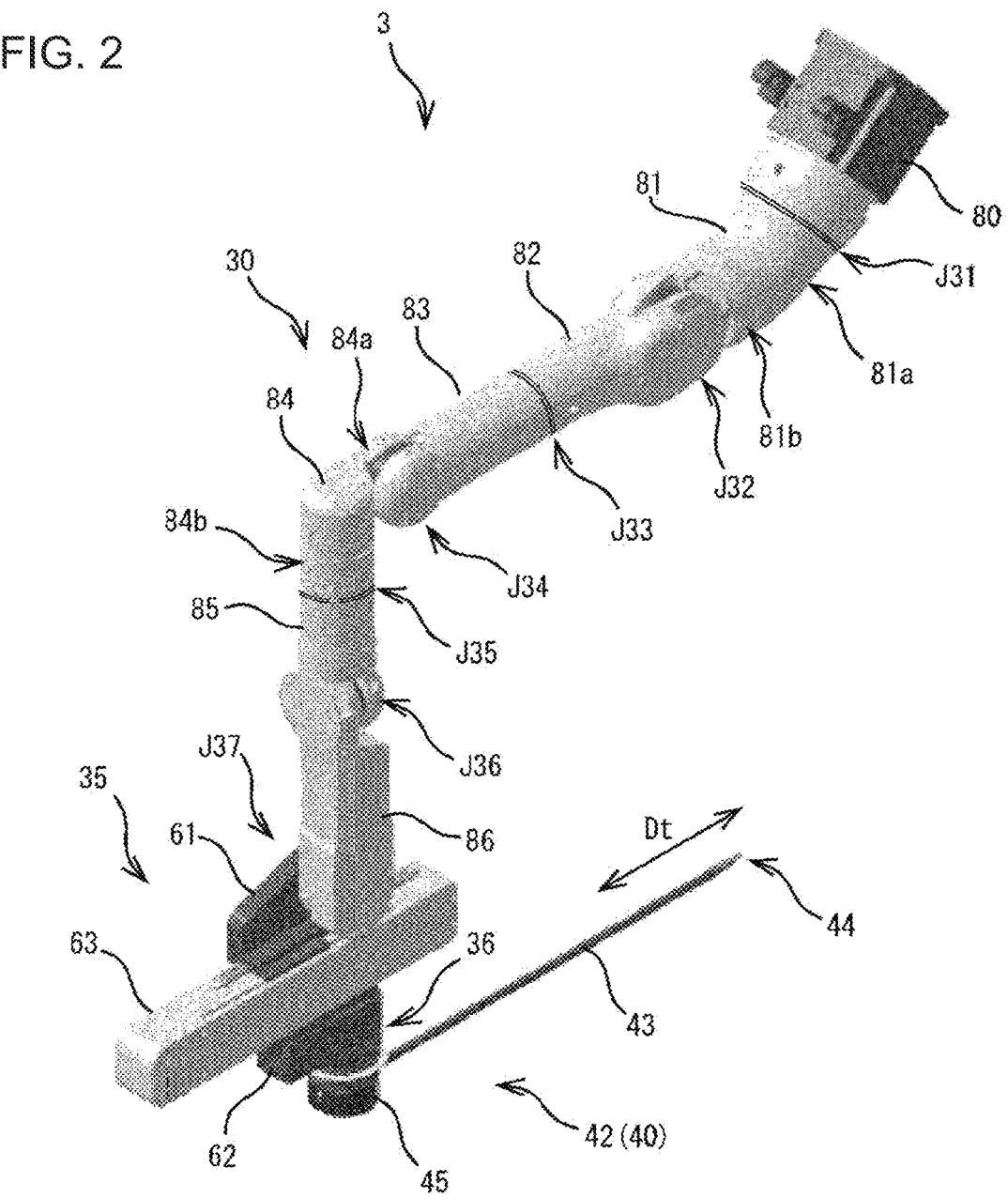
FIG. 2 is a diagram illustrating a schematic view of an overall configuration of a manipulator arm of the surgical system illustrated in FIG. 1.

FIG. 2 is a schematic view of an overall configuration of the manipulator arm of the surgical system illustrated in FIG. 1. FIG. 2 illustrates a schematic configuration of a single arm 3 to which the instrument 42 is attached, the single arm 3 being out of the multiple arms 3 provided to the patient-side system 1. In this embodiment, the arms 3 provided to the patient-side system 1 have the same or similar configurations; however, at least one of the arms 3 may have a different configuration from the other arms (for example, may have different degrees of freedom, or the like). As illustrated in FIG. 2, the arm 3 includes an arm body 30 and a translation mechanism 35 connected to the distal end portion of the arm body 30. The arm 3 is formed such that the distal end portion thereof is three-dimensionally movable with respect to the corresponding proximal end portion. The distal end portion of the arm 3 is provided with the tool holding part 36 that can hold the surgical tool 40 (the instrument 42 or the endoscope assembly). The tool holding part 36 is provided with four rotation drive parts respectively engaged with four rotation members provided in a drive unit 45 of the surgical tool 40, wherein each of the rotation drive parts includes built-in motors M39. In an embodiment, the tool holding part 36 is provided to the translation mechanism 35.

The instrument 42 includes the drive unit 45 provided to the proximal end portion thereof, an end effector (procedure tool) 44 provided to the distal end portion, and an elongated shaft 43 connecting the drive unit 45 and the end effector 44. The drive unit 45, the shaft 43, and the end effector 44 are arranged along an axis direction Dt or a longitudinal direction of the instrument 42. The drive unit 45 includes the four rotation members engaged with the four rotation drive parts of the tool holding part 36, and is configured to transmit rotation of each of the rotation members to the end effector 44 through an elongate element(s) such as a cable(s), a rod(s) or the like The end effector 44 of the instrument 42 is selected from a group including a surgical tool having a movable joint (for example, pair of forceps, pair of scissors, grasper, needle holder, micro dissector, staple applier, tacker, suction and irrigation tool, snare wire, clip applier, and so on) and a surgical tool having no joints (for example, cutting blade, ablation probe, irrigation device, catheter, suction orifice, and so on). In this disclosure, an "surgical tool" includes both a camera and a lighting constituting the endoscope assembly and the instruments.

When the arm 3 is the instrument arm, the tool holding part 36 detachably holds the instrument 42. The shaft 43 of the instrument 42 held by the tool holding part 36 extends along the axis direction Dt. On the other hand, when the arm 3 is the camera arm, the tool holding part 36 detachably holds the endoscope assembly. Note that the tool holding part 36 provided to the camera arm has the same shape or configuration as that of the tool holding part 36 provided to the instrument arm, however, may have a different shape or configuration from that of the tool holding part 36 provided to the instrument arm.

The arm 3 is configured to be attachable to and detachable from the arm base 5. The arm 3 has resistances for irrigation processing and sterile processing, including water resistance, heat resistance, and chemical resistance. There are various ways for the sterile processing of the arm 3. For example, autoclave sterilization, EOG sterilization, chemical sterilization with an antiseptic, and so on may be selectively used.

The arm body 30 includes a base 80 detachably attached to the arm base 5 and arm link portions sequentially connected with each other from the base 80 toward the distal end portion. With one arm link portion rotatably connected to another arm link portion sequentially, the arm 3 forms multiple joint portions. The arm link portions include the first link 81 to a seventh link 87. The joint portions include the first joint J31 to a seventh joint J37. Each of the joint portions in this embodiment is formed of a rotation joint having a rotation axis; however, at least a part of the joint portions may be formed of a direct-acting joint.

More specifically, the proximal end portion of the first link 81 is connected to the distal end portion of the base 80 with the first joint J31 as a roll joint arranged therebetween. The proximal end portion of the second link 82 is connected to the distal end portion of the first link 81 with the second joint J32 as a pivotal joint arranged therebetween. The proximal end portion of the third link 83 is connected to the distal end portion of the second link 82 with the third joint J33 as a roll joint arranged therebetween. The proximal end portion of the fourth link 84 is connected to the distal end portion of the third link 83 with the fourth joint J34 as a pivotal (pitch) joint arranged therebetween. The proximal end portion of the fifth link 85 is connected to the distal end portion of the fourth link 84 with the fifth joint J35 as a roll joint arranged therebetween. The proximal end portion of the sixth link 86 is connected to the distal end portion of the fifth link 85 with the sixth joint J36 as a pivotal joint arranged therebetween. The proximal end portion of the translation mechanism 35 is connected to the distal end portion of the sixth link 86 with the seventh joint J37 as a pivotal joint arranged therebetween. Thus, the arm 3 is formed as a multi-axis joint (seven-axis joint) arm having the multi-degree of freedom (seven degrees of freedom). Consequently, the arm 3 can change the overall orientation thereof without changing the position and orientation of the distal end portion of the arm 3.

In this embodiment, the first link 81 has a bending shape between the joints J31 and J32 next to each other. In other words, the first link 81 is formed such that the rotation axis of the first joint J31 and the rotation axis of the second joint J32 do not cross each other. That is, the first link 81 includes a first portion 81a and a second portion 81b. The first portion 81a extends in a predetermined first direction (a rotation axis direction of the first joint J31) from the first joint J31 on the proximal end side. The second portion 81b extends in a second direction crossing the extending direction of the first portion 81a (the second direction also being a direction orthogonal to the second joint J32) from the distal end portion of the first portion 81a to be connected to the second joint J32 on the distal end side. An angle formed by the first direction and the second direction at the first link 81 is, for example, 120 degrees or more and 160 degrees or less (for example, 140 degrees). The first portion 81a and the second portion 81b are smoothly connected with each other. This makes it possible to easily arrange wires (not illustrated) such as electric wirings in the arm link portions although one of the arm link portions has the bending shape.

In addition, the fourth link 84 has a bending shape between the joints J34 and J35 next to each other. In other words, the fourth link 84 is formed such that the rotation axis of the fourth joint J34 and the rotation axis of the fifth joint J35 do not cross each other. That is, the fourth link 84 includes a first portion 84a and a second portion 84b. The first portion 84a extends in a first direction (a direction orthogonal to both the rotation axis of the fourth joint J34 and the rotation axis of the fifth joint J35) from the fourth joint J34 on the proximal end side. The second portion 84b extends in a second direction crossing the extending direction of the first portion 84a (a rotation axis direction of the fifth joint J35) from the distal end portion of the first portion 84a to be connected to the fifth joint J35 on the distal end side. An angle formed by the first direction and the second direction at the fourth link 84 is, for example, 70 degrees or more and 110 degrees or less (for example, 90 degrees). The first portion 84a and the second portion 84b are smoothly connected with each other.

Figure 3:
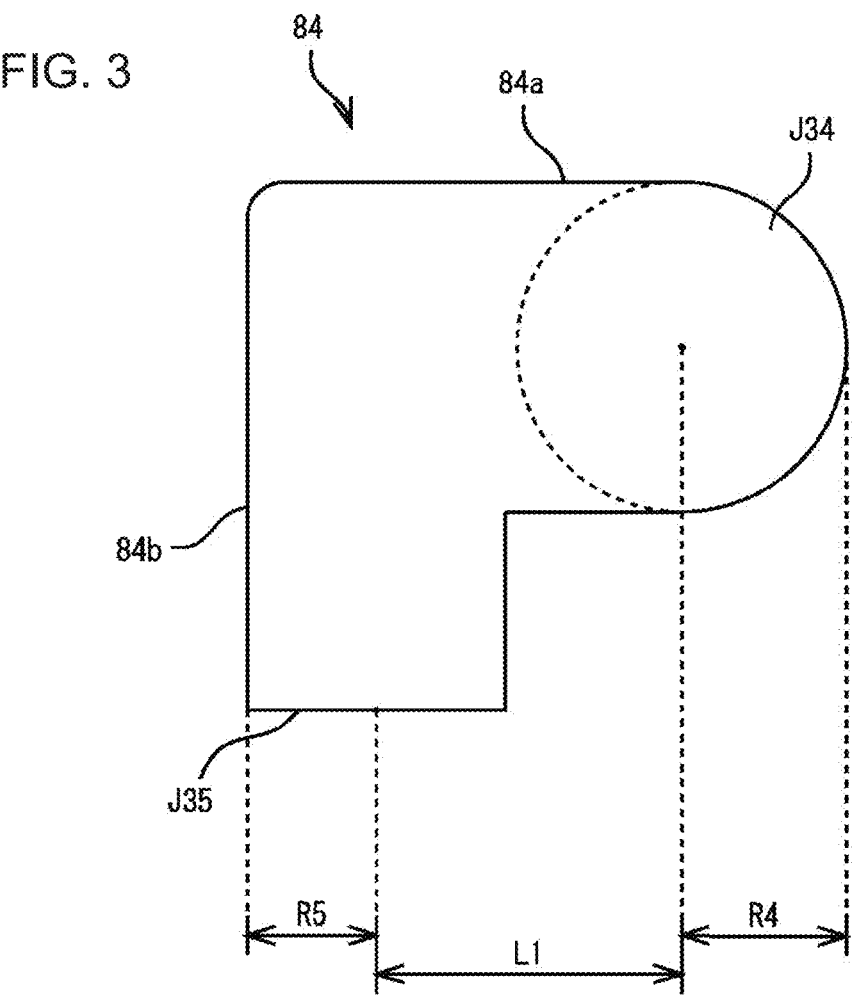
FIG. 3 is a diagram illustrating a side view schematically illustrating an example of a fourth link illustrated in FIG. 2.

Specifically, the fourth link 84 is formed to have the link length shorter than those of the other joint portions. FIG. 3 is a side view schematically illustrating an example of the fourth link 84 illustrated in FIG. 2. As illustrated in FIG. 3, for example, the fourth link 84 is formed such that a length L1 in the first direction between the rotation axis of the fourth joint J34 and the rotation axis of the fifth joint J35 is no more than four times, or more preferably no more than three times, of a radius R4 of the fourth joint J34 or a radius R5 of the fifth joint J35. The radius R4 of the fourth joint J34 is defined as a distance between the rotation axis of the fourth joint J34 and a position of the proximal end portion of the fourth link 84 in the first direction. The radius R5 of the fifth joint J35 is defined as a distance between the rotation axis of the fifth joint J35 and a position of the distal end portion of the fourth link 84 in the first direction. The fourth link 84 is formed such that the length L1 is no more than two times of the sum of the radius R4 of the fourth joint J34 and the radius R5 of the fifth joint J35. More preferably, the above-described length L1 is shorter than a length obtained by adding the radius R5 of the fifth joint J35, which is the shorter one between the radius R4 of the fourth joint J34 and the radius R5 of the fifth joint J35, to the sum of the radius R4 of the fourth joint J34 and the radius R5 of the fifth joint J35.

The other links 82, 83, 85, and 86 are each formed in a straight line shape between the joint portions next to each other. In other words, the other links 82, 83, 85, and 86 are formed such that the rotation axes of the joint portions next to each other cross each other.

The arm link portions are formed such that one arm link portion has the smaller area of a cross section orthogonal to the longitudinal direction than that of the other arm link portion (or the base 80) connected on the proximal end side of the one arm link portion. Accordingly, the arm 3 is formed to be gradually narrower from the proximal end portion toward the distal end portion. In addition, the joints J32, J34, and J36 as the pivotal joints are formed as follows. The distal end portion of each of the arm link portions 81, 83, and 85 on the proximal end side is positioned on one side in the rotation axis direction relative to a middle portion in the rotation axis direction in the corresponding joint portion. Meanwhile, the proximal end portion of each of the arm link portions 82, 84, and 86 on the distal end side is positioned on the other side in the rotation axis direction relative to the middle portion in the rotation axis direction in the corresponding joint portion, such that the proximal end portions of the arm link portions 82, 84, and 86 face the distal end portions of the arm link portions 81, 83, and 85, respectively. That is, these joints J32, J34, and J36 are formed by the halved joint.

Besides, a width of each joint portion in the rotation axis direction is shorter than a diameter (the maximum dimension) of a cross section of a portion closer to the proximal end portion of corresponding one of the arm link portions 81, 83, and 85 on the proximal end side, the cross section being orthogonal to the longitudinal direction. The width of the joint portion is a distance between an outer end portion in the rotation axis direction of the distal end portion of corresponding one of the arm link portions 81, 83, and 85 on the proximal end side and an outer end portion in the rotation axis direction of the proximal end portion of corresponding one of the arm link portions 82, 84, and 86 on the distal end side.

As described above, each joint portion and the arm link portion on the distal end side of the joint portion is formed narrower than the arm link portion on the proximal end side. This makes it possible to increase a moving range of the arm 3 (a range in which the arm 3 does not interfere with the other) in a work space that becomes narrower as the arm 3 comes closer to the surgery site 110 of the patient P.

An outer shell of the arm body 30 is formed of a member having heat resistance and chemical resistance, such as mainly stainless. An opening portion of the arm body 30 such as an inspection hole is covered with a resin cover. With the cover formed of a member such as resin, it is possible to achieve weight reduction of a portion that does not contribute the strength of the arm 3. Consequently, it is possible to reduce the accidental impact caused when the cover falls off or when the arm 3 hits another arm 3 or the surgical assistant O, for example. The outer shell itself of the arm body 30 may include a portion formed of a resin member. A connection portion between the links is provided with sealing (not illustrated) to provide water resistance. The sealing has the heat resistance for autoclaved sterilization and the chemical resistance for antiseptic. In the connection portion between the links, an end portion of one link is inserted into an end portion of the other link to be connected with the one link, and the sealing is arranged so as to fill the space between the end portions of the links. Thus, the sealing is hidden from external appearance. In this way, entering of water, chemical liquid, and vapor through the space between the sealing and the link is suppressed.

The translation mechanism 35 is provided at the distal end portion of the arm 3. The translation mechanism 35 is a mechanism that translationally moves the instrument 42 attached to the tool holding part 36 in the extending direction of the shaft 43 by translationally moving the tool holding part 36 attached to the distal end portion of the translation mechanism 35 in the axis direction Dt.

Figure 6:
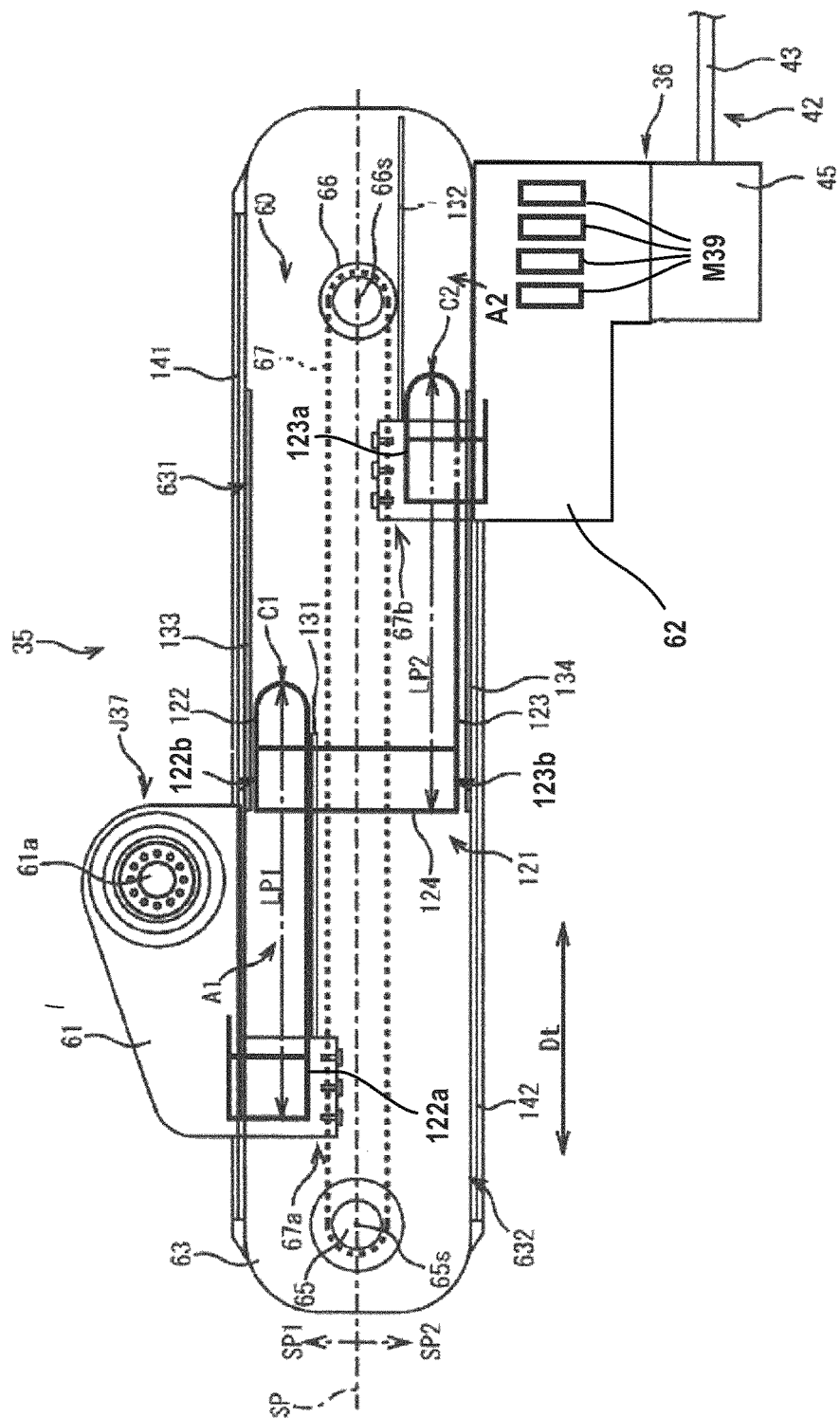
FIG. 6 is a diagram illustrating a view of an internal configuration of the connection unit of the translation mechanism according to one or more embodiments.

The translation mechanism 35 includes a proximal side unit 61 that is connected to the distal end portion of the sixth link 86 of the arm body 30, serving as the distal end portion of the arm 3, with the seventh joint J37 as a pivotal joint arranged therebetween, a distal side unit 62, a connection unit 63 that moves the proximal side unit 61 and the distal side unit 62 in an interlocking manner, and an interlocking mechanism 60 provided in the connection unit 63 (see FIG. 6 described later). The seventh joint J37 extends in a direction orthogonal to the axis direction Dt. A drive source of the translation mechanism 35 is provided to the connection unit 63. The connection unit 63 extends along the axis direction Dt.

In the translation mechanism 35, the interlocking mechanism 60 allows changings of relative positions of the proximal side unit 61 and the connection unit 63 in the axis direction Dt and relative positions of the connection unit 63 and the distal side unit 62 in the axis direction Dt, so as to change a position of the instrument 42 attached to the tool holding part 36 provided to the distal side unit 62 in the axis direction Dt with respect to the proximal side unit 61. Note that the detail configuration of the translation mechanism 35 is described later.

Figure 4:
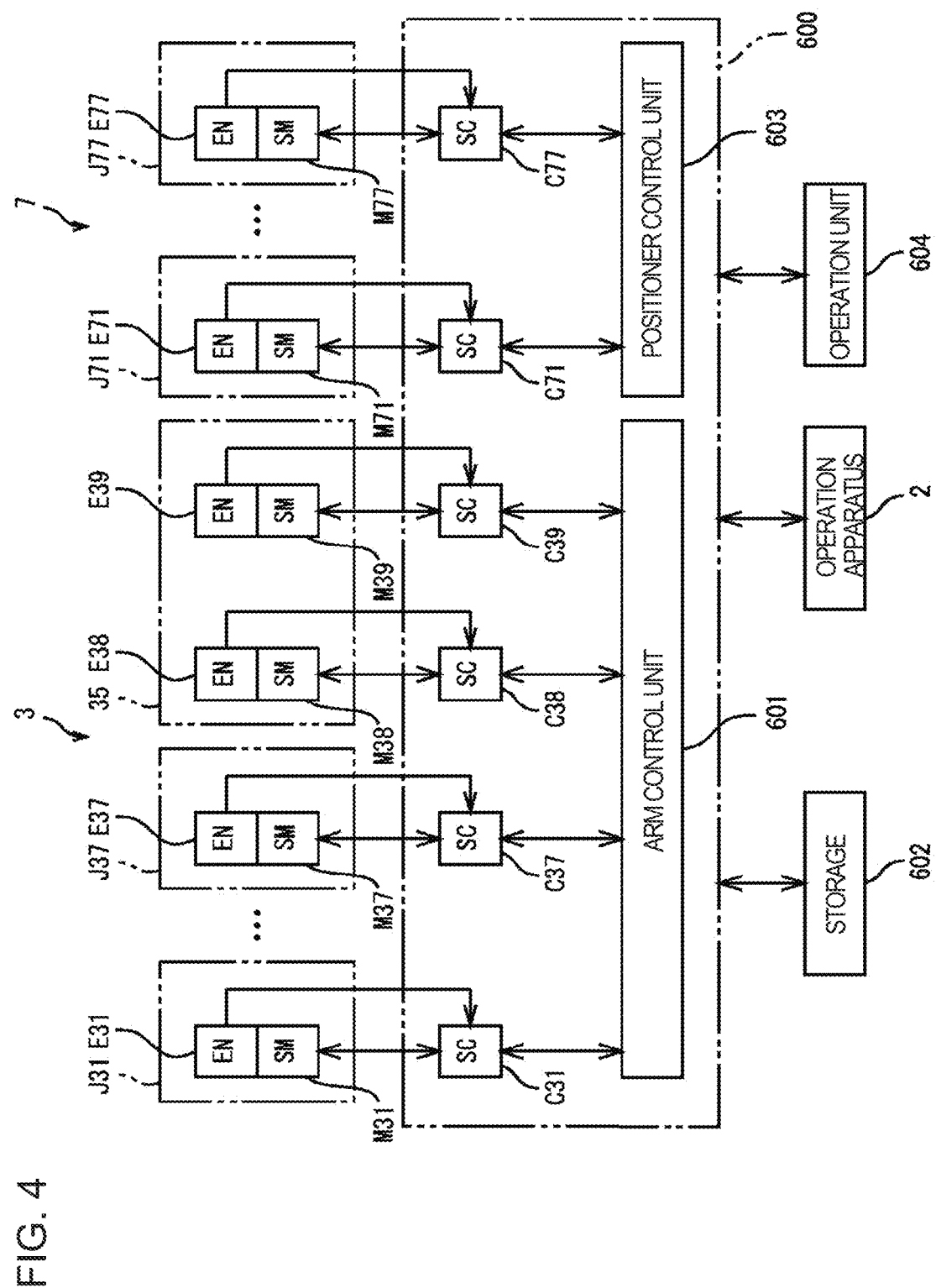
FIG. 4 is a block diagram illustrating a view of a schematic configuration of a control system of the manipulator arm of the surgical system illustrated in FIG. 1.

FIG. 4 is a block diagram illustrating a schematic configuration of a control system of the manipulator arm of the surgical system illustrated in FIG. 1. The arm body 30 having the above-described configuration is provided with driving servomotors (indicated as SM in FIG. 4) M31 to M37, encoders (indicated as EN in FIG. 4) E31 to E37 detecting rotation angles of the servomotors M31 to M37, and reduction drives (not illustrated) reducing the outputs of the servomotors M31 to M37 to increase the torque, with each corresponding to the joints J31 to J37 of the arm 3. Likewise, the positioner 7 is provided with driving servomotors M71 to M77, encoders E71 to E77 detecting rotation angles of the servomotors M71 to M77, and reduction drives (not illustrated) reducing the outputs of the servomotors M71 to M77 to increase the torque, with each corresponding to the joints J71 to J77 of the positioner 7.

Among the joints J31 to J37 and J71 to J77 in FIG. 4, the control systems of the first joint J31 and the seventh joint J37 of the arm 3 and the control systems of the first joint J71 and the seventh joint J77 of the positioner 7 are illustrated as a representative, and the control systems of the other joints J33 to J36 and J72 to J76 are omitted. In addition, a translation mechanism 35 is provided with a servomotor M38 to rotate a first pulley 65 (described later) for the translational movement, four servomotors M39 (only one of the servomotors M39 is illustrated to simplify the illustration in FIG. 4) to rotate four rotation members in the drive unit 45 of the surgical tool 40, encoders E38 and E39 detecting rotation angles of the servomotors M38 and M39, and reduction drives (not illustrated) reducing the outputs of the servomotors M38 and M39 to increase the torque.

The encoders E31 to E39 and E71 to E77 are provided as an example of rotation position detection units for detecting the rotation positions (the rotation angles) of the servomotors M31 to M39 and M71 to M77. Rotation position detection units such as resolvers may be used instead of the encoders E31 to E39 and E71 to E77. The above-described elements of the drive systems of the arm 3 and wirings and control units for the elements are made of high-temperature resistant materials and have the heat resistance for sterile processing.

The controller 600 includes an arm control unit 601 that controls the movements of the arms 3 based on the action instructions and a positioner control unit 603 that controls the movement of the positioner 7. Servo-control units C31 to C39 are electrically connected to the arm control unit 601, and the servomotors M31 to M39 are electrically connected to the arm control unit 601 via not-illustrated amplifier circuits and the like. Likewise, servo-control units C71 to C77 are electrically connected to the positioner control unit 603, and the servomotors M71 to M79 are electrically connected to the positioner control unit 603 via not-illustrated amplifier circuits and the like.

In the above-described configuration, based on the action instruction inputted to the operation apparatus 2 during procedure, a position and orientation instruction of the distal end portion of the arm 3 is inputted to the arm control unit 601. Based on the position and orientation instruction, the arm control unit 601 generates position instruction values for the servomotors M31 to M39 and outputs the thus-generated position instruction values to the corresponding servo-control units C31 to C39. The servo-control units C31 to C39 receive the position instruction values, and then generate drive instruction values (torque instruction values) based on the rotation angles detected by the encoders E31 to E39 and the received position instruction values and output the thus-generated drive instruction values. The amplifier circuits receive the drive instruction values, and then supply drive currents corresponding to the received drive instruction values to the servomotors M31 to M39. As described above, the servomotors M31 to M39 are servo-controlled such that the distal end portion of the arm 3 is set at the position and orientation corresponding to the position and orientation instruction. Further, based on the action instruction inputted to the operation unit 604 before the surgery, a position and orientation instruction of the distal end portion of the positioner 7 is inputted to the positioner control unit 603. Like the arm control unit 601, the positioner control unit 603 controls the position and orientation of the positioner 7 based on the position and orientation instruction.

The controller 600 includes a storage 602 that can read out data to the arm control unit 601. The storage 602 stores in advance surgery information. The surgery information includes information that indicates what types of the arms 3 are to be used together in surgery.

The storage 602 stores information such as the length of a surgical tool (the endoscope assembly or the instrument) held by the distal end portion of the arm 3 along the axis direction Dt. This allows the arm control unit 601 to grasp the position of the distal end portion of the surgical tool held by the distal end portion of the arm 3 based on the position and orientation instruction of the distal end portion of the arm 3.

Figure 5:
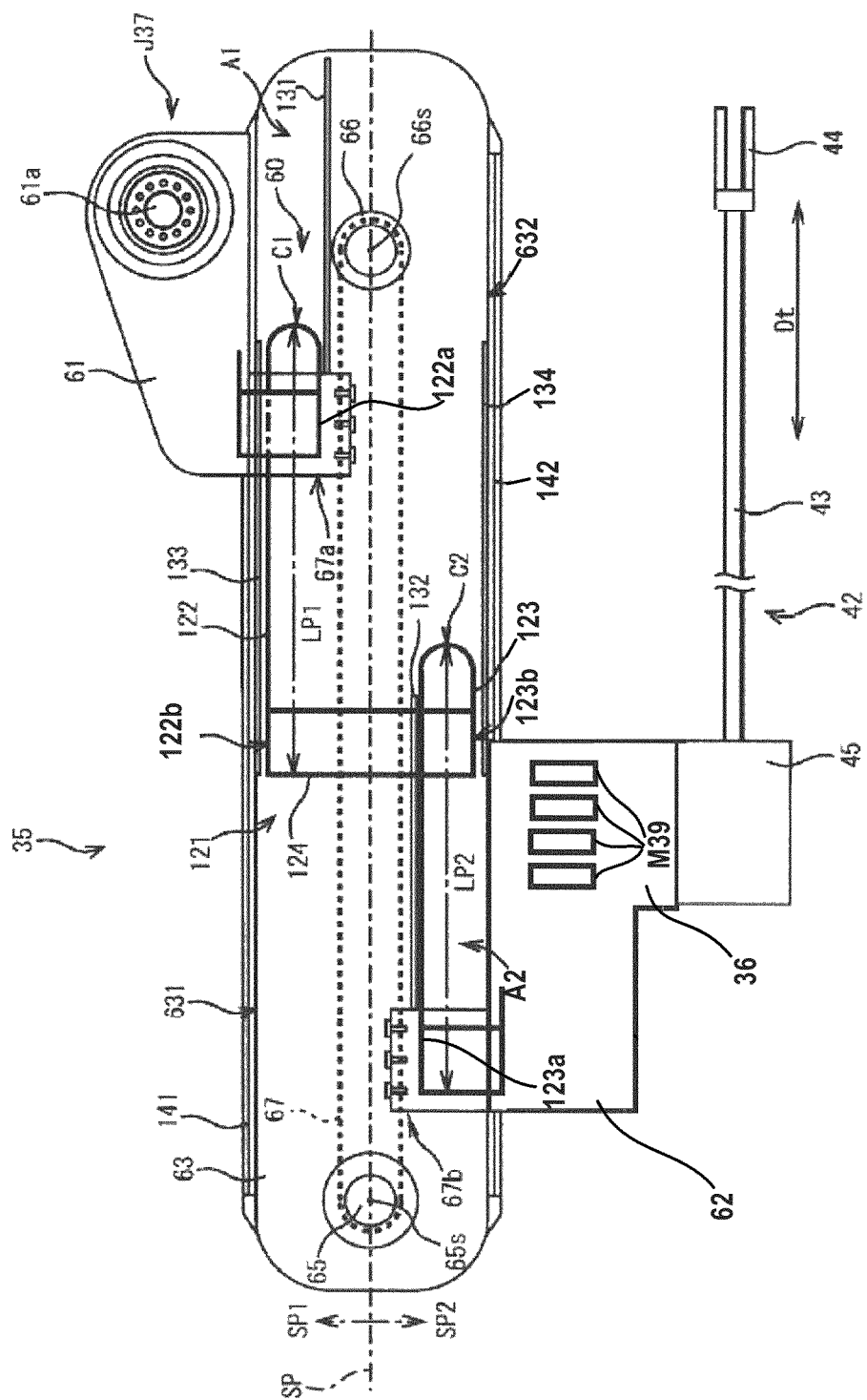
FIG. 5 is a diagram illustrating a view of an internal configuration of a connection unit of a translation mechanism according to one or more embodiments.

Next, the translation mechanism 35 according to one or more embodiments is described in detail. FIG. 5 and FIG. 6 are diagrams illustrating views of an internal configuration of the connection unit of the translation mechanism 35 according to one or more embodiments, wherein FIG. 5 illustrates a contracted state and FIG. 6 illustrates an expanded stated of the translation mechanism.

The connection unit 63 includes a first wall part 631, and a second wall part 632 to which the distal side unit 62 is slidably attached in the longitudinal direction Dt. The proximal side unit 61 is attached to the first wall part 631 to be slidable in the longitudinal direction Dt with respect to the first wall part 631. The distal side unit 62 is attached to the second wall part 632 to be slidable in the longitudinal direction Dt with respect to the second wall part 632. The proximal side unit 61 and the first wall part 631 are connected to each other through a first slide mechanism 141 such that the proximal side unit 61 and the first wall part 631 are relatively movable in the longitudinal direction Dt. Similarly, the second wall part 632 and the distal side unit 62 are connected to each other through a second slide mechanism 142 such that the second wall part 632 and the distal side unit 62 are relatively movable in the longitudinal direction Dt.

The interlocking mechanism 60 includes: a first pulley 65 serving as a driving pulley, rotatably supported by the connection unit 63; a second pulley 66, serving as a driven pulley, rotatably supported by the connection unit 63; and the belt member 67 formed of an endless belt and wound around the first and second pulleys 65 and 66. In an embodiment, the first pulley 65 is provided at a position in the connection unit 63 on a side of the proximal end of the instrument 42 in the longitudinal direction Dt and the second pulley 66 is provided at a position in the connection unit 63 on a side of the distal end of the instrument 42 in the longitudinal direction Dt.

The proximal side unit 61 is attached to a first attachment position 67a of the belt member 67, which is a position on an linear portion (e.g. an upper linear part) of the belt member 67 on a first side SP1 with reference to a plane SP, which includes a rotational axis 65s of the first pulley 65 and a rotational axis 66s of the second pulley 66. The distal side unit 62 is attached to a second attachment position 67b of the belt member 67, which is a position on a linear portion (e.g. a lower linear part) of the belt member 67 on second side SP2, which is opposite to the first side SP1, with reference to the plane SP. The distal side unit 62 is attached to the second attachment position 67b of the belt member 67 so as to move in the direction opposite to the movement direction of the proximal side unit 61 by the movement of the belt member 67.

The first attachment position 67a and the second attachment position 67b of the belt member 67 are set on the belt member 67 such that when the first attachment position 67a is moved closer to one of the first pulley 65 and the second pulley 66, the second attachment position 67b is moved closer to the other of the first pulley 65 and the second pulley 66 than to the one. For example, in the contracted state such as being illustrated in FIG. 5, the first attachment position 67a is positioned close to the second pulley 66, and the second attachment position 67b is positioned close to the first pulley 65. On the other hand, in the expanded state such as being illustrated in FIG. 6, the first attachment position 67a is positioned close to the first pulley 65, and the second attachment position 67b is positioned close to the second pulley 66.

A direction from the first pulley 65 toward the second pulley 66 is defined as a first direction. When the first pulley 65 rotates clockwise, the first attachment position 67a of the belt member 67 moves in the first direction and approaches the second pulley 66, and the second attachment position 67b of the belt member 67 moves a second direction opposite to the first direction and approaches the first pulley 65. On the other hand, when the first pulley 65 rotates counterclockwise, the first attachment position 67a of the belt member 67 moves in the second direction and approaches the first pulley 65, and the second attachment position 67b of the belt member 67 moves in the first direction and approaches the second pulley 66. Accordingly, when the proximal side unit 61 is moved from a position close to the second pulley 66 to a position close to the first pulley 65, the distal side unit 62 is moved from a position close to the first pulley 65 to a position close to the second pulley 66.

That is, when each of the proximal side unit 61 and the distal side unit 62 is moved with respect to the connection unit 63 by a distance between the first pulley 65 and the second pulley 66, one of the proximal side unit 61 and the distal side unit 62 is relatively moved with respect to the other of the proximal side unit 61 and the distal side unit 62 by about twice the distance between the first pulley 65 and the second pulley 66. In other words, the interlocking mechanism 60 functions as a double speed mechanism that makes a movement speed (or a relative positional change) of the proximal side unit 61 with respect to the distal side unit 62 twice as a movement speed (or a relative positional change) of the proximal side unit 61 with respect to the connection unit 63.

The translation mechanism 35 further includes an electrical wiring circuit 121 provided in the connection unit 63 and making an electrical connection between the proximal side unit 61 and the distal side unit 62.

The electrical wiring circuit 121 includes a first flexible printed wiring part (e.g. substrate) 122, a second flexible printed wiring part (e.g. substrate) 123, and a connecting wiring part 124. The seventh joint J37, which is provided between the sixth link 86 and the proximal side unit 61 of the translation mechanism 35, includes, at the center portion thereof, a through hole 61a through which electrical wiring (not illustrated) passes. That is, the electrical wiring (electrical cable(s) or the like) wired in the arm 3 is introduced through the through hole 61a into the proximal side unit 61. The electrical cable(s) introduced through the through hole 61a in the proximal side unit 61 is connected to a proximal end portion of the first flexible printed wiring part 122. With this, the electrical power and the control signals from the electrical wiring wired through the wagon 70, the positioner 7, the arm base 5, and the arm 3 are supplied to the electrical wiring circuit 121 of the translation mechanism 35.

The second flexible printed wiring part 123 is electrically connected to the distal side unit 62 in order to drive the servomotor M39. With this, the electrical power and the control signals from the electrical wiring wired through the arm 3 are supplied through the electrical wiring circuit 121 of the translation mechanism 35 to the distal side unit 62.

The first flexible printed wiring part 122 is fixed to the proximal side unit 61 at a first fixation position 122a, which is the same position as the first attachment position 67a of the proximal side unit 61 in movement directions of the belt member 67. The first flexible printed wiring part 122 extends from the first fixation position 122a in a first direction from the first pulley 65 toward the second pulley 66, is bent and folded (turned-back) at the middle thereof (first bended part C1) in a circular arc shape (e.g. a U or C shape) with maintaining the restoring force thereof, extends from the first bended part C1 in a second direction opposite to the first direction, and fixed to the connection unit 63 at a second fixation position 122b between the first pulley 65 and the second pulley 66.

The second flexible printed wiring part 123 is fixed to the distal side unit 62 at a third fixation position 123a, which is the same position as the second attachment position 67b of the distal side unit 62 in the movement directions of the belt member 67. The second flexible printed wiring part 123 extends from the third fixation position 123a in the first direction, is bent and folded (turned-back) at the middle thereof (second bended part C2) in a circular arc shape (e.g. U or C shape) with maintaining the restoring force thereof, and fixed to the connection unit 63 at a fourth fixation position 123b between the first pulley 65 and the second pulley 66.

More specifically, the first flexible printed wiring part 122 extends from the first fixation position 122a in the direction toward the second pulley 66, and the first bended part C1 of the first fixable printed wring part 122 has a convex shape projected toward the second pulley 66 (toward the distal end side of the instrument 42, or toward a side to which the translation mechanism 35 extends). Similarly, the second fixable printed wiring part 123 extends from the third fixation position 123a in the direction toward the second pulley 66, and the second bended part C2 of the second fixable printed wiring part 123 has a convex shape projected toward the second pulley 66 (toward the distal end side of the instrument 42, or toward a side to which the translation mechanism 35 extends). The second fixation position 122b is a position where the first flexible printed wiring part 122 is attached to the connection unit 63 on the first surface SP1 side of the plane SP. The fourth fixation position 123b is a position where the second flexible printed wiring part 123 is attached to the connection unit 63 on the second surface Sp2 side of the plane SP, opposite to the first surface SP1 side. That is, the second fixation position 122b is opposed to the fourth fixation position 123b across the plane SP.

The connecting wiring part 124 electrically connects the second fixation position 122b of the first flexible printed wiring part 122 and the fourth fixation position 123b of the second flexible printed wiring part 123. The connecting wiring part 124 is provided between the first pulley 65 and the second pulley 66. In an example illustrated in FIGS. 5 and 6, the connecting wiring part 124 is positioned at the central portion between the first pulley 65 and the second pulley 66. The servomotor M38 for driving the first pulley 65 is built in the connecting unit 63. The connecting wiring part 124 is electrically connected to the servomotor M38 that drives the first pulley 65, and the servomotor M38 is energized with the electrical power supplied through the electrical wiring circuit 121 and is controlled in response to the control signals supplied through the electrical wiring circuit 121.

The first flexible printed wiring part 122 and the second flexible printed wiring part 123 are configured such that the bended portions C1 and C2 having their restoring forces are moved in the extending direction (the longitudinal direction Dt) of the belt member 67 in response to the positional relationship between the first attachment position 67a and the second attachment position 67b.

Both of the bended portions C1 and C2 with the restoring forces of the first flexible printed wiring part 122 and the second flexible printed wiring part 123 are moved between the positions close to the second pulley 66 and the positions close to the connecting wiring part 124 (the second pulley 66 side of the connecting wiring part 124).

For example, in the contracted state illustrated in FIG. 5, when the first attachment position 67a is positioned in the vicinity of the second pulley 66 and the second attachment position 67b is positioned in the vicinity of the first pulley 65, the first bended part C1 is positioned in the vicinity of the second pulley 66 and the second bended part C2 is positioned in the vicinity of the connecting wiring part 124. On the other hand, in the expanded state illustrated in FIG. 6, when the first attachment position 67a is positioned in the vicinity of the first pulley 65 and the second attachment position 67b is positioned in the vicinity of the second pulley 66, the first bended part C1 is positioned in the vicinity of the connecting wiring part 124 and the second bended part C2 is positioned in the vicinity of the second pulley 66.

The connection unit 63 includes, between the first wall part 631 and the belt member 67, a first space A1 in which the first flexible printed wiring part 122 is accommodated. The connection unit 63 further includes, between the second wall part 632 and the belt member 67, a second space A2 in which the second flexible printed wiring part 123 is accommodated.

The first space A1 is defined by an inner surface of the first wall part 631 and a first guide member 131, wherein the first guide member 131 is opposed to the inner surface of the first wall part 631 and extends in the extending direction of the belt member 67. The second space A2 is defined by an inner surface of the second wall part 632 and a second guide member 132, wherein the second guide member 132 is opposed to the inner surface of the second wall part 632 and extends in the extending direction of the belt member 67. Note that with respect to the direction parallel to the rotational axes 65s and 66s of the pulleys 65 and 66, the first space A1 and the second space A2 are defined by a pair of side walls (not illustrated) orthogonal to the first and second wall parts 631 and 632.

The connection unit 63 further includes a third guide member 133 extending in the extending direction of the belt member 67 along the inner surface of the first wall part 631 and a fourth guide member 134 extending in the extending direction of the belt member 67 along the inner surface of the second wall part 632. The third guide member 133 is fixed to the inner surface of the first wall part 631. The fourth guide member 134 is fixed to the inner surface of the second wall part 632. Thus, the first space A1 is defined by the first guide member 131 and the third guide member 133 and the second space A2 is defined by the second guide member 132 and the fourth guide member 134.

With this configuration, the first flexible printed wiring part 122 is provided in the first space A1 defined by the first guide member 131 and the third guide member 133, and the movements of the first flexible printed wiring part 122 is guided by the first guide member 131 and the third guide member 133. The second flexible printed wiring part 123 is provided in the second space A2 defined by the second guide member 132 and the fourth guide member 134, and the movements of the second flexible printed wiring part 123 is guided by the second guide member 132 and the fourth guide member 134. This can reduce the volume of wiring spaces of the flexible printed wiring parts 122 and 123 while maintaining smooth movements of the flexible printed wiring parts 122 and 123.

The first guide member 131 is attached to the belt member 67 at the first attachment position 67a. Accordingly, the first guide member 131 is moved along with the movements of the proximal side unit 61 in the extending direction of the belt member 67. The second guide member 132 is attached to the belt member 67 at the second attachment position 67b. Accordingly, the second guide member 132 is moved along with the movements of the distal side unit 62 in the extending direction of the belt member 67.

A part of the first flexible printed wiring part 122 between the first fixation position 122a and the first bended part C1 is located in the vicinity of or in contact with the first guide member 131. Thus, such a part of the first flexible printed wiring part 122 is guided by the first guide member 131. As the proximal side unit 61 is moved from the position in the vicinity of the second pulley 66 (see FIG. 5) to the position in the vicinity of the first pulley 65 (see FIG. 6), an area of the first flexible printed wiring part 122 that is contactable with the first guide member 131 increases. However, in such a movement, the first flexible printed wiring part 122 does not slide against the first guide member 131, since the first guide member 131 is moved together with the proximal side unit 61. In other words, even when the proximal side unit 61 is moved, the positional relationship between the part of the first flexible printed wiring part 122 and the first guide member 131 along the extending direction of the belt member 67 is not changed.

Similarly, a part of the second flexible printed wiring part 123 between the third fixation position 123a and the second bended part C2 is located in the vicinity of or in contact with the second guide member 132. Thus, such a part of the first flexible printed wiring part 122 is guided by the second guide member 132. As the distal side unit 62 is moved from the position in the vicinity of the second pulley 66 (see FIG. 6) to the position in the vicinity of the first pulley 65 (see FIG. 5), an area of the second flexible printed wiring part 123 that is contactable with the second guide member 132 increases. However, in such a movement, the second flexible printed wiring part 123 does not slide against the second guide member 132, since the second guide member 132 is moved together with the distal side unit 62. In other words, even when the distal side unit 62 is moved, the positional relationship between the part of the second flexible printed wiring part 123 and the second guide member 132 in the extending direction of the belt member 67 is not changed.

The part of the first flexible printed wiring part 122 between the first bended part C1 and the second fixation position 122b is located in the vicinity of or in contact with the third guide member 133. Thus, such a part of the first flexible printed wiring part 122 is guided by the third guide member 13. As the proximal side unit 61 is moved from the position in the vicinity of the first pulley 65 (see FIG. 6) to the position in the vicinity of the second pulley 66 (see FIG. 5), an area of the first flexible printed wiring part 122 that is contactable with the third guide member 133 increases. However, in such a movement, the first flexible printed wiring part 122 does not slide against the third guide member 133, because the second fixation position 122b fixed to the connection unit 63 does not move (that is, the second fixation position 122b relatively moves together with the connection unit 63 as seen from the proximal side unit 61). In other words, even when the proximal side unit 61 is moved, the positional relationship between the part of the first flexible printed wiring part 122 and the third guide member 133 in the extending direction of the belt member 67 is not changed.

Similarly, a part of the second flexible printed wiring part 123 between the second bended part C2 and the fourth fixation position 123b is located in the vicinity of or in contact with the fourth guide member 134. Accordingly, such a part of the second flexible printed wiring part 123 is guided by the fourth guide member 134. As the distal side unit 62 is moved from the position in the vicinity of the first pulley 65 (see FIG. 5) to the position in the vicinity of the second pulley 66 (see FIG. 6), an area of the second flexible printed wiring part 123 that is contactable with the fourth guide member 134 increases. However, in such a movement, the second flexible printed wiring part 123 does not slide against the fourth guide member 134, because the fourth fixation position 123b fixed to the connection unit 63 does not move (that is, the fourth fixation position 123b relatively moves together with the connection unit 63 as seen from the distal side unit 62). In other words, even when the distal side unit 62 is moved, the positional relationship between the part of the second flexible printed wiring part 123 and the fourth guide member 134 in the extending direction of the belt member 67 is not changed.

Accordingly, when the proximal side unit 61 and the distal side unit 62 moves relative to the connection unit 63, the guide members 131 to 134 does not slide against the corresponding flexible printed wiring parts 1222 and 123. Therefore, the flexible printed wiring parts 122 and 123 is appropriately guided by the guide members 131 to 134 while preventing the flexible printed wiring parts 122 and 123 from being in slide-contact with the guide members 131 to 134, so as to prevent wear of the flexible printed wiring parts 122 and 123.

The length of the first guide member 131 is set based on a distance from the proximal end (the first fixation position 122a) of the first flexible printed wiring part 122 and the apex of the first bended part C1 in the state (FIG. 6) where the proximal side unit 61 (the first attachment position 67a) is located in the position closest to the first pulley 65. Similarly, the length of the second guide member 132 is set based on a distance from the apex of the second bended part C2 of the second flexible printed wiring part 123 to the distal end (the third fixation position 123a) of the second flexible printed wiring part 123, in the state (FIG. 5) where the distal side unit 62 (the second attachment position 67b) is located at the position closest to the first pulley 65.

The length of the third guide member 133 is set based on a distance from the apex of the first bended part C1 of the first flexible printed wiring part 122 to the distal end (the second fixation position 122b) of the first flexible printed wiring part 122, in the state (FIG. 5) where the proximal side unit 61 (the first attachment position 67a) is located in the position closest to the second pulley 66. Similarly, the length of the fourth guide member 134 is set based on a distance from the proximal end (the fourth fixation position 123b) of the second flexible printed wiring part 123 to the apex of the second bended part C2 of the second flexible printed wiring part 123 in the state (FIG. 6) where the distal side unit 62 (the second attachment position 67b) is located in the position closest to the second pulley 66.

Figure 7:
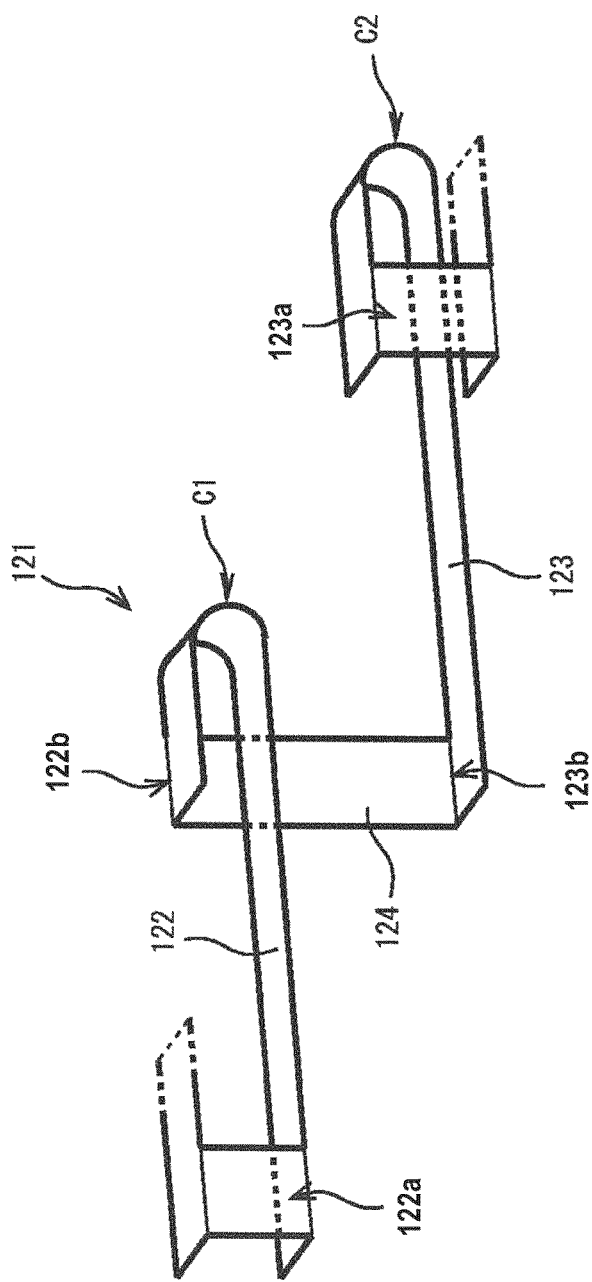
FIG. 7 is a diagram illustrating a schematic view of an electrical wiring circuit in an expanded state such as being illustrated in FIG. 6.

FIG. 7 is a diagram illustrating a schematic view of an electrical wiring circuit in the expanded state such as being illustrated in FIG. 6. In FIG. 7, configurations of the translation mechanism 35 other than the electrical wiring circuit 121 (the first flexible printed wiring part 122, the second flexible printed wiring part 123, and the connecting wiring part 124) is omitted. The first flexible printed wiring part 122, the second flexible printed wiring part 123, and the connecting wiring part 124 are formed of a single sheet of a flexible printed wiring substrate configured to be bent at the second fixation position 122b and the fourth fixation position 123b.

Thus, the connecting wiring part 124 extends along the side wall of the connection unit 63. The electrical wiring circuit 121 formed of the single flexible printed wiring substrate is fixed to the connection unit 63 by engaging and locking the connecting wiring part 124 with the connection unit 63.

A connection portion of the first flexible printed wiring part 122 to the proximal side unit 61 is formed of a portion extended and bent from the first fixation position 122a, which is extended from the base portion, in the longitudinal direction, of the first flexible printed wiring part 122 in the widthwise direction of the first flexible printed wiring part 122. Similarly, a connection portion of the second flexible printed wiring part 123 to the distal side unit 62 is formed of a portion extended and bent from the third fixation position 123a, which is extended from the base portion, in the longitudinal direction, of the second flexible printed wiring part 123 in the widthwise direction of the second flexible printed wiring part 123.

The flexible printed wiring substrate may be also referred to as FPC (Flexible Printed Circuit), and, for example, may be configured to have a thin insulation base member (base film) having an insulation property such as polyimide or the like and a wiring and/or a circuit formed of a conductive metal(s) such as a copper or the like attached on the base member. Therefore, the flexible printed wiring substrate is thin and have flexible and resilient properties of the base member to restore the shape thereof to the original flat shape when being bent in an arc shape or the like. Thus, the shapes of the first flexible printed wiring part 122 and the second flexible printed wiring part 123 are uniquely changed based on the positional relationships between the fixation positions 122b and 123b and the attachment positions 67a and 67b.

According to the configurations described above, the first flexible printed wiring part 122, the connecting wiring part 124, and the second flexible printed wiring part 123, functioning as the electrical wiring to electrically connect the proximal side unit 61 and the distal side unit 62, are provided in the connection unit 63, in which the belt member 67 wound around the first pulley 65 and the second pulley 66 is accommodated.

The first flexible printed wiring part 122 provided between the proximal side unit 61 and the connection unit 63 is bent in the arc shape at the first bended part C1 with maintaining the restoring force. The second flexible printed wiring part 123 provided between the distal side unit 62 and the connection unit 63 is also bent in the arc shape at the second bended part C2 with maintaining the restoring force.

With this configuration, when the proximal side unit 61 is relatively moved with respect to the connection unit 63 and the distal side unit 62 is relatively moved with respect to the connection unit 63, the arc shaped portions (the bended portions C1 and C2) of the first flexible printed wiring part 122 and the second flexible printed wiring part 123 are moved in the extending direction of the belt member 67 (the longitudinal direction Dt). This can minimize the volume for electrical wiring in the connection unit 63 without hindering the translation movements of the proximal side unit 61 and the distal side unit 62. Therefore, this can prevent growing in size of the translation mechanism 35 while providing the electrical wiring in the translation mechanism 35.

Further, according to the configurations described above, the electrical wiring in the translation mechanism 35 is formed of the single flexible printed wiring substrate. This can simplify the structure of thereof and can reduce the volume needed for electrical wiring.

In an embodiment, the entire length of the first flexible printed wiring part 122 from the proximal end through the bended portion C1 to the distal end is the same as the entire length of the second flexible printed wiring part 123 from the proximal end through the bended portion C2 to the distal end. Further, the first flexible printed wiring part 122 and the second flexible printed wiring part 123 in the bent shapes have the same length along the extending direction (the longitudinal direction Dt) of the belt member 67, regardless of the positional relationship between the first attachment position 67a and the second attachment position 67b.

More specifically, the distance LP1 from the apex of the first bended part C1 of the first flexible printed wiring part 122 and an end (the first fixation position 122a or the second fixation position 122b) of the first flexible printed wiring part 122 farther from the first bended part C1 is always equal to the distance LP2 from the apex of the second bended part C2 of the second flexible printed wiring part 123 to an end (the third fixation position 123a or the fourth fixation position 123b) of the second flexible printed wiring part 123 farther from the second bended part C2, regardless of the contracted state illustrated in FIG. 5, the expanded stated illustrated in FIG. 6, and states between FIG. 5 and FIG. 6.

With this, the design of the first flexible printed wiring part 122 and the design of the second flexible printed wiring part 123 can be the same. Further the first flexible printed wiring part 122 and the second flexible printed wiring part 123 are moved in the same manner, and thus lengths of life of both parts 122 and 123 are approximately the same. This can facilitate maintenance of the electrical wiring in the translation mechanism 35.

Therefore, the translation mechanism 35 according to one or more embodiments has an appropriate or a preferable configuration as a translation mechanism provided to the arm 3 used in the surgical system 100.

According to the above descriptions, many improvements and modifications of the above one or more embodiments are apparent to the person skilled in the art. Thus, the above descriptions should be construed as only an example, and the above descriptions are provided for teaching one or more aspects for executing the invention to the person skilled in the art. It is possible to practically change the details of the configuration and/or function of the above described one or more embodiments without departing from the spirit of the invention.

In one or more embodiments described above, the first flexible printed wiring part 122 and the second flexible printed wiring part 123 of the electrical wiring circuit 121 are projected at the bended portions C1 and C2 in the convex shape protruding toward the distal end side of the instrument 42 (toward the second pulley 66 side), however, the invention is not limited to this. For example, the first flexible printed wiring part 122 and the second flexible printed wiring part 123 of the electrical wiring circuit 121 may be projected in a convex shape toward the proximal end side of the instrument 42 (toward the first pulley 65 side).

In one or more embodiments described above, the first flexible printed wiring part 122, the connecting wiring part 124, and the second flexible printed wiring part 123 of forming the electrical wiring circuit 121 are formed of the single flexible printed wiring substrate, however, the invention is not limited to this. For example, the first flexible printed wiring part 122 and the second flexible printed wiring part 123 may be separated from each other. In this case, the connecting wiring part 124 may be formed of a flexible printed wiring substrate or may be formed of wiring structure (electrical cable(s) or the like) other than the flexible printed wiring substrate.

In one or more embodiments described above, the guide members 131 to 134 that guide the flexible printed wiring parts 122 and 123 is provided in the connection unit 63, however, the invention is not limited to this. For example, the first guide member 131 and the second guide member 132 may be provided without providing the third guide member 133 and the fourth guide member 134 or all the guide members 131 to 134 may not be provided.

In one or more embodiments described above, the single connection unit 63 is provided in the translation mechanism 35, however a plurality of connection units 63 may be provided. For example, two connection units may be provided between the proximal side unit 61 and the distal side unit 62. In this case, each of the two connection units may include the interlocking mechanism 60, such that the proximal side unit 61 and a second connection unit may be attached to a belt member 67 in a first connection unit, while the first connection unit and the distal side unit 62 may be attached to a belt member 67 in the second connection unit. The configuration of an electrical wiring circuit 121 in each of the first connection unit and the second connection unit may be the same as the electrical wiring circuit 121 of the connection unit 63 according to one or more embodiments described above.

Further, in each of the arms 3 and/or the positioners 7, the numbers of the joints and the links (the number of the degrees of the freedom) and the shapes of the joints and the links are not limited to the above described one or more embodiments and various aspects can be employed therefor.

The configurations described above is useful to improve the linear movement speed of the surgical tool while preventing complication of the configuration of the translation mechanism.

The invention claimed is:

1. A manipulator arm for a surgery system, comprising:
an arm body including a plurality of links and a plurality of joints; and
a translation mechanism provided to a distal end portion of the arm body, wherein
the translation mechanism includes:
a proximal side unit connected to the distal end portion of the arm body;
a distal side unit including a tool holding part to which a surgical tool is attached and which includes a motor configured to drive the surgical tool;
a connection unit connecting the proximal side unit and the distal side unit; and
an electrical wiring circuit electrically connecting the proximal side unit and the distal side unit, wherein
the connection unit includes a first pulley; a second pulley; and an endless belt member wound around the first and second pulleys and movable in a first direction from the first pulley toward the second pulley and a second direction opposite to the first direction, and
the proximal side unit is attached to the endless belt member at a first attachment position, and the distal side unit is attached to the endless belt member at a second attachment position in such a manner that the distal side unit moves in a direction opposite to a direction in which the proximal side unit moves in association with movements of the endless belt member.

2. The manipulator arm according to claim 1, wherein the proximal side unit and the distal side unit are attached to the endless belt member in such a manner that when the distal side unit is located at a position closest to one of the first pulley and the second pulley, the proximal side unit is located at a position closest to the other of the first pulley and the second pulley.

3. The manipulator arm according to claim 1, wherein the electrical wiring circuit comprises a flexible printed wiring part.

4. The manipulator arm according to claim 1, wherein the proximal side unit is connected to the distal end portion of the arm body via a pivotal joint.

5. The manipulator arm according to claim 1, wherein the connection unit includes a motor to drive one of the first and second pulleys.

6. The manipulator arm according to claim 5, wherein the connection unit includes the electrical wiring circuit so that the motor to drive one of the first and second pulleys is connected.

7. The manipulator arm according to claim 1, wherein the electrical wiring circuit comprises:
a first flexible printed wiring part extending in the first direction from a first fixation position at which the first flexible printed wiring part is fixed to the proximal side unit, curved to form a first bended part, and extending from the first bended part to a second fixation position at which the first flexible printed wiring part is fixed to the connection unit between the first pulley and the second pulley;
a second flexible printed wiring part extending in the first direction from a third fixation position at which the second flexible printed wiring part is fixed to the distal side unit, curved to form a second bended part, and extending from the second bended part to a fourth fixation position at which the second flexible printed wiring part is fixed to the connection unit between the first pulley and the second pulley; and
a connecting wiring part electrically connecting the first flexible printed wiring part and the second flexible printed wiring part.

8. The manipulator arm according to claim 7, wherein positions of the first bended part and the second bended part are changed in response to change of a positional relationship between the distal side unit and the proximal side unit in association with the movements of the endless belt member.

9. The manipulator arm according to claim 7, wherein the first flexible printed wiring part, the second flexible printed wiring part, and the connecting wiring part are made up of a single flexible printed wiring substrate that is bent.

10. The manipulator arm according to claim 7, wherein a first length from the first fixation position to the first bended part of the first flexible printed wiring part is same as a second length from the fourth fixation position to the second bended part of the second flexible printed wiring part.

11. The manipulator arm according to claim 10, wherein when a positional relationship between the first fixation position and the second fixation position is changed in association with the movements of the endless belt member, the first length and the second length are changed while maintaining the first length and the second length to be the same.

12. The manipulator arm according to claim 7, wherein the connection unit includes:
a first wall part to which the proximal side unit is attached to be slidable with respect to the first wall part;
a second wall part to which the distal side unit is attached to be slidable with respect to the second wall part;
a first space in which the first flexible printed wiring part is accommodated between the first wall part and the endless belt member; and
a second space in which the second flexible printed wiring part is accommodated between the second wall part and the endless belt member, wherein
the first space is defined by an inner surface of the first wall part and a first guide member provided opposed to the inner surface of the first wall part,
the second space is defined by an inner surface of the second wall part and a second guide member provided opposed to the inner surface of the second wall part,
the first guide member is attached to the endless belt member at the first attachment position, and
the second guide member is attached to the endless belt member at the second attachment position.

13. The manipulator arm according to claim 7, wherein the second fixation position is opposite to the fourth fixation position across a plane including rotational axes of the first and second pulleys.

14. A patient-side system for a surgery system comprising:
a manipulator arm;
a wheeled base configured to hold the manipulator arm, wherein
the manipulator arm comprises:
an arm body including a plurality of links and a plurality of joints; and
a translation mechanism provided to a distal end portion of the arm body, wherein
the translation mechanism includes:
a proximal side unit connected to the distal end portion of the arm body;
a distal side unit including a tool holding part to which a surgical tool is attached and which includes a motor configured to drive the surgical tool;
a connection unit connecting the proximal side unit and the distal side unit; and
an electrical wiring circuit electrically connecting the proximal side unit and the distal side unit, wherein
the connection unit includes a first pulley; a second pulley; and an endless belt member wound around the first and second pulleys and moveable in a first direction from the first pulley toward the second pulley and a second direction opposite to the first direction, and the proximal side unit is attached to the endless belt member at a first attachment position, and the distal side unit is attached to the endless belt member at a second attachment position in such a manner that the distal side unit moves in a direction opposite to a direction in which the proximal side unit moves in association with movements of the endless belt member.

15. The patient-side system according to claim 14, wherein
the proximal side unit and the distal side unit are attached to the endless belt member in such a manner that when the distal side unit is located at a position closest to one of the first pulley and the second pulley, the proximal side unit is located at a position closest to the other of the first pulley and the second pulley.

16. The patient-side system according to claim 14, wherein
the electrical wiring circuit comprises a flexible printed wiring part.

17. The patient-side system according to claim 14, further comprising:
an arm base holding a proximal end portion of the manipulator arm; and
a positioner held by the wheeled base and including a multi-axis robot arm configured to move the arm base.

18. The patient-side system according to claim 14, wherein
the connection unit includes a motor to drive one of the first and second pulleys.

19. The patient-side system according to claim 14, wherein
the electrical wiring circuit comprises:
a first flexible printed wiring part extending in the first direction from a first fixation position at which the first flexible printed wiring part is fixed to the proximal side unit, curved to form a first bended part, and extending from the first bended part to a second fixation position at which the first flexible printed wiring part is fixed to the connection unit between the first pulley and the second pulley;
a second flexible printed wiring part extending in the first direction from a third fixation position at which the second flexible printed wiring part is fixed to the distal side unit, curved to form a second bended part, and extending from the second bended part to a fourth fixation position at which the second flexible printed wiring part is fixed to the connection unit between the first pulley and the second pulley; and
a connecting wiring part electrically connecting the first flexible printed wiring part and the second flexible printed wiring part.

20. The patient-side system according to claim 19, wherein
the first flexible printed wiring part, the second flexible printed wiring part, and the connecting wiring part are made up of a single flexible printed wiring substrate that is bent.

* * * * *